United States Patent [19]
Peterson

[11] Patent Number: 5,839,509
[45] Date of Patent: Nov. 24, 1998

[54] METHOD AND APPARATUS FOR GATHERING LIQUID SAMPLE USING A SUBMERSIBLE PUMP

[76] Inventor: Roger Peterson, Country Rd. 375, Old Ocean, Tex. 77463

[21] Appl. No.: 795,147

[22] Filed: Feb. 7, 1997

Related U.S. Application Data

[63] Continuation-in-part of Ser. No. 692,018, Aug. 2, 1996.

[51] Int. Cl.$^6$ ..................................................... E21B 43/12
[52] U.S. Cl. ................................ 166/264; 166/68; 166/72
[58] Field of Search .................................. 166/53, 64, 68, 166/72, 370, 372, 105

[56] References Cited

U.S. PATENT DOCUMENTS

| | | | |
|---|---|---|---|
| 4,546,830 | 10/1985 | McLaughlin et al. | 166/64 X |
| 4,585,060 | 4/1986 | Bernardin et al. | 166/64 |
| 4,625,801 | 12/1986 | McLaughlin et al. | 166/53 X |
| 5,261,348 | 11/1993 | Niehaus et al. | 166/64 |
| 5,373,897 | 12/1994 | Skarvan | 166/53 |

*Primary Examiner*—Frank Tsay
*Attorney, Agent, or Firm*—Gunn & Associates, P.C.

[57] ABSTRACT

This invention is directed toward apparatus and methods for gathering liquid samples from a reservoir of liquid using a submersible pump and subsequently retrieving the samples for analysis. The invention is more specifically directed toward the gathering and preparing of water samples for analysis for tritium content, where the samples are collected from underground formations penetrated by a borehole or collected at varying depths in surface canals and the like. The samples are subsequently transferred to the surface of the earth for analysis. The submersible pump is operated by means of a surface valving system and a valving system mounted on the submersible pump. The pump inlet valve is set to open or "crack" at a predetermine pressure, however the pump is not filled until a vacuum is applied to the pump. After filling, the pump is purged thereby transporting the sampled liquid to the surface by applying pressure. Vacuum and pressure are supplied to the submerged pump by means of a surface vacuum/compressor system. No electrical valves or electrical power sources are required in the submersible pump.

40 Claims, 4 Drawing Sheets

METHOD AND APPARATUS FOR GATHERING LIQUID SAMPLE USING A SUBMERSIBLE PUMP

BACKGROUND OF THE INVENTION

This application is a continuation-in-part of U.S. patent application Ser. No. 692,018 filed on Aug. 2, 1996.

FIELD OF THE INVENTION

This invention is directed toward apparatus and methods for gathering liquid samples using a submersible pump and subsequently preparing liquid samples for analysis, and more specifically directed toward the gathering and preparing of water samples for analysis for tritium content, where the samples are collected from underground formations penetrated by a borehole or collected at varying depths in surface ponds, canals and the like.

BACKGROUND OF THE ART

The monitoring of liquid samples for contaminants is quite common in today's industrialized society. Such monitoring is carried out to track the efficiency of various manufacturing processes. In addition, such monitoring is employed to monitor potential hazards to humans and to the environment resulting from various manufacturing and processing operations.

Many types of nuclear manufacturing and processing facilities were built in significant numbers starting in the late 1940's and early 1950's. In the following decades, even more such facilities were built world wide as a result of the proliferation nuclear power, nuclear weaponry, and nuclear medicine. As with most manufacturing and processing operations, nuclear facilities generate wastes which can be hazardous to the environment and to the human and animal population, and such wastes must be monitored and disposed using methods which minimize health and environmental risks.

Attention is now directed toward nuclear facilities designed for the manufacture of nuclear weapons. More particularly, attention is directed toward "fission" weapon facilities used to produced weapons based upon induced neutron "chain" reactions in certain isotopes of uranium and plutonium. Great quantities of energy are released as a result of the induced chain reaction which is often referred to as an "atomic explosion". It is well known that one precursor for such an energy release or explosion is a "critical mass" of the fission material in order to sustain the chain reaction. Weapons designers also found in the 1940's that more efficient energy releases or explosion could be obtained if the chain reaction were initiated with a burst of neutrons from a device known in the art as a "trigger".

Several techniques have been used in nuclear weapons to construct triggers which produce large neutron fluxes for relatively short periods of time. The most common trigger is based upon the reaction $$H^2 + H^3 = He^4 + n$$

where $H^2$=deuterium which is a hydrogen atom with a nucleus containing a neutron as well as a proton;

$H^3$=tritium which is a hydrogen atom with a nucleus containing two neutrons as well as a proton;

$He^4$=helium; and n=a neutron.

That is, when tritium is bombarded with deuterium at a sufficient energy, a nuclear reaction occurs which yields helium, plus a neutron with approximately 14 million electron volts (MeV) of energy. Triggers based upon this "deuterium-tritium" reaction therefore produce the neutron flux desired as a trigger for fission type weapons.

Tritium is used at fission type weapons manufacturing facilities and, as might be expected, most of these manufacturing facilities produce significant amounts of tritium. Tritium is radioactive with a half life of approximately 12.33 years, and decays to ground state $He^3$ by the emission of a beta particle. Tritium reacts chemically as "normal" hydrogen ($H^1$). It is well known that hydrogen is easily ingested by plant life and animal life including humans. Tritium is likewise easily ingested, but tritium ingestion results in the possible chemical binding of radioactive tritium within the plant or animal organism. As an example, tritium ingested by a human would result in radioactive tritium atoms being chemically bound or "lodged" within the human. Subsequently, as the tritium decays with a half life of 12.33 year, beta particles are emitted at the sites of the bound tritium causing significant biological and cellular damage in the area of emission. It is apparent, therefore, that waste liquid, such as water which is contaminated with tritium, can be a significant health threat to humans and to the environment. Such tritium contaminated water can be found in cooling ponds and drainage canals in the vicinity of nuclear facilities such as nuclear weapons plants. Furthermore, run-off water, which migrates and percolates into the earth around nuclear facilities, can also be contaminated with tritium. This becomes an especially critical problem if these contaminated waters migrate into drinking water aquifers. The result is a potable aquifer contaminated with a beta emitting tritium with a half life of 12.33 years.

Nuclear sites are currently monitored for tritium wastes. Liquid samples such as water are collected at varying depths from cooling ponds or canals. To monitor the migration of tritium contaminated water toward the water tables, test wells are often drilled about the site, ground water is allowed to flow into each of these wells, and water samples are taken at varying depths within the well. As an example, the detection of tritium contamination in a water sample gathered near the surface usually indicates that contaminated water has not migrated to deeper aquifers. Furthermore, the combination of tritium concentration measurements made at multiple depths in multiple wells can be used to generate a three dimensional map of any tritium contamination in the ground beneath the nuclear facility. Since nuclear facilities can be quite large and cover hundreds if not thousands of acres, it should be understood that tens or even hundreds of monitor wells are required to properly monitor water movement and possible ground water contamination.

Again examining current tritium monitoring techniques, liquid samples gathered from monitor wells, or at different depths within surface ponds or canals, must be pretreated prior to analysis for tritium. In one such pretreatment, the water is passed through a column containing a plurality of resin materials in order to remove certain cations and other materials which prohibit accurate tritium concentration measurements. This pretreatment can be performed at the sample site, but, using current technology, is preferably performed at a remote, analytical laboratory under controlled conditions. Tritium analysis is currently being performed at the remote, analytical laboratory. The time required to perform this type of analysis often takes one to two months from the time samples are received. The analysis cost per sample is also quite high. Considering that multiple sample sites such as monitor wells are needed, and that samples should be taken at varying depths at each sample site, the total cost of a monitor survey can be quite high. Furthermore, it is highly desirable to sample at a given site, such as a monitor well, as many as three to four times per day in order to detect early any tritium contamination so that remedial actions can be taken immediately. Although sampling at this time frequency can be done today, the current sample analysis turnaround of one to two months negates the usefulness of this method.

One object of the present invention is to provide apparatus and methods for efficiently obtaining liquid samples at multiple sample sites and at multiple depths at each site. This is accomplished by a novel submersible pump system which can quickly be filled and which can quickly transfer sample to the surface from varying depth within the liquid. Sample liquid is acquired and transferred to the surface by means of valves cooperating with a surface compression and vacuum system. No electrical power or solenoid valves are required downhole to operate the pump.

Another object of the present invention is to provide apparatus and methods for efficiently treating, at the sample site, the samples obtained at varying locations and varying depths. This is accomplished by a valving system cooperating with a controller system such that the required sample is obtained, treated, and provided to an analyzing system upon command.

A further object of the invention is to provide apparatus and methods so that each sample site can be sampled at varying depth three to four time per day, and that these samples can be pretreated prior to analysis.

Still another object of the present invention is to provide apparatus and methods for pretreating and analyzing a sample such that the concentration of tritium within the sample can be obtained, at the sample site, within thirty minutes after initiation of the pretreating and analysis steps.

A additional object of the invention is to provide apparatus and methods for gathering, pretreating, and analyzing water samples for tritium content completely under the control of a microprocessor controller and timer, and without human intervention.

There are other objects and applications of the present invention which will become apparent in the following disclosure.

SUMMARY OF THE INVENTION

The invention is directed toward apparatus and methods for gathering liquid samples using a submersible pump set to open at or above predetermined head pressures when a vacuum is applied to the pump, and the subsequent preparation of these samples for analysis for elements or compounds within the liquid samples. Although applicable to a variety of liquids and to a variety of elements or compounds, the preferred embodiment of the invention is directed toward the gathering and pretreating of water samples for tritium analysis. This disclosure is further directed toward apparatus and methods for the gathering or collecting of water samples from underground formations penetrated by a borehole, or collecting water samples at varying depths in surface canals, ponds, and the like. The invention is particularly suited for monitoring water in the vicinity of nuclear manufacturing, fabrication and disposal facilities for tritium contamination of ground waters.

The sampling system includes submersible pumps and a vacuum/compressor system and valving system for operating these pumps in order to gather liquid samples at varying depth below the surface of the earth, and transporting these samples to the surface of the earth for pretreatment prior to analysis for contaminants. The pumps are designed to operate at a predetermined liquid head pressure, and the pump is filled with liquid only when this head pressure is exceeded and only when a vacuum is applied to the pump using the vacuum side of the vacuum/compressor system. Pump filling can, therefore, be initiated on command by applying a vacuum to the pump once the pump is positioned below a predetermined depth within the liquid column. Once the pump is filled, the liquid is then transferred to the surface of the earth by applying pressure from the pressure side of the vacuum/compressor system. No electrical power or solenoid valves are required downhole to operate the pump. For purposes of discussion, it will be assumed that the liquid is water and that the water contaminant is tritium.

Although the system can be used to sample only one location, one of its main advantages is that multiple locations can be sequentially sampled or "monitored" for tritium contamination. As mentioned previously, the system can be used to obtain samples from below the surface, such as water samples from subterranean wells, from cooling ponds, canals and the like. Again, for purposes of discussion, it will be assumed that the water samples are being obtained at varying depths in a plurality of well boreholes. Each well is preferably lined or "cased" with a steel, plastic or composite liner to prevent the respective boreholes from caving in. A submersible pump is positioned within each well, and water samples from each well are taken by the submersible pumps sequentially and automatically under the control of a microprocessor and timer. The valving system of each submersible pump includes a spring loaded check valve which can be set to operate at above a certain hydraulic pressure. This, in turn, allows a given pump to obtain a water sample only below a given depth corresponding to the selected hydrostatic pressure. This feature allows sampling at varying, preselected depths as will be discussed in detain is a subsequent section of this disclosure.

Samples from each pump, and therefore samples from each well, are transferred or "evacuated" to the surface for pretreating and analysis. The compressor/vacuum pump system cooperating with a valving system, which also includes flow lines, is used to transfer the samples to the surface. Specifics of the operation of the valving system will subsequently be presented in detail. At this point, it suffices to say that the vacuum/compressor system and the valving system, under the control of the microprocessor and timer, are used to control the flow of the sample water. Furthermore, these systems are also used to flow purge air and wash water within the sample in order to clean the system between sampling sequences so that the next sample will not be contaminated by the previous sample.

The valving system cooperates with a carousel mechanism which holds a plurality of columns in which sample water is pretreated prior to analysis for tritium. The carousel mechanism is operated mechanically by cylinder and piston devices powered by the compressor/vacuum pump system under the control of a carousel controller which, in turn, is under control of the system microprocessor and timer. This feature of the invention greatly increases the speed and automation of the pretreatment phase of the sampling and analysis process.

Once each collected water sample has been treated in a specific sample pretreatment column held by the carousel mechanism, the sample is then passed to an analyzer for analysis by means of the valving system and its accompanying flow lines. This transfer is also under control of the system microprocessor and timer, which cooperates with the analyzer by means of communication signals. Tritium concentration is preferably measured with a chromatographic analyzer such as a Radiomatic HPLC high precision liquid chromatographic unit. Results of each sample analysis are displayed with an appropriate analog or digital meter, printed by means of a printer, or recorded on a magnetic disk or other digital recording device.

All of the previously discussed elements of the system, with the exception of the submersible pumps and some elements of the valving system and flow lines, are preferably located at the surface of the earth.

The plurality of submersible pumps used in the invention rapidly and automatically obtain samples and transfer these samples to the surface for pretreatment and analysis. The pumps are also automatically purged with some fluid after sample transfer such that the next sample will not be contaminated by the previous sample.

The invention also provides rapid and automatic means for pretreating each sample prior to analysis by using the carousel mechanism in cooperation with the valving system and the system microprocessor and timer. This means increases the accuracy and precision of the overall analysis method, while reducing cost by eliminating the need for manual sample pretreatment. Furthermore, the samples can be pretreated on site thereby reducing the overall sampling and analysis time when compared with current methods.

The valving system of the submersible pumps is such that each sample site can be sampled at varying depth. Furthermore, the system microprocessor and timer can be programmed so that multiple samples are obtained sequentially in time from the same well at the same depth. The sampling sequence is initiated when a vacuum is applied to the pump. Since the entire sampling and pretreatment system is fast, efficient and automatic, each well can be sampled and analyzed at the same depth as often as three to four time per day. This makes the system ideally suited for monitoring tritium at facilities where contamination can be sudden. As an example, using a four time per day sampling, the maximum time interval between samples is six hour. Since sample pretreating and analysis is done on site in approximately thirty minutes, the maximum time that can elapse after contamination such as a spill is slightly more than six hours. This rapid detection capability of the invention permits rapid remedial action to be taken, especially when compared with typical one to two month sample analysis turnaround times of present, off site, commercial tritium analysis services.

In summary, the sequence of sample acquisition and sample pretreatment events, described briefly above, are controlled by the system microprocessor and timer thereby eliminating need for direct human operation. This substantially reduces the cost and increases the accuracy of sampling and pretreating compared to present human operated systems. The entire sampling, pretreatment and analysis sequence requires less than thirty minutes thereby analysis results to be obtained very rapidly when compared with present, commercial, off site tritium analysis services. The entire sampling and pretreatment system is relatively small and portable, as is the preferred analyzer. Sample analysis can therefore be obtained on site within thirty minutes compared with the typical one to two month turn-around of present, commercial, off site analysis services.

BRIEF DESCRIPTION OF THE DRAWINGS

So that the manner in which the above recited features, advantages and objects of the present invention are attained and can be understood in detail, more particular description of the invention, briefly summarized above, may be had by reference to embodiments thereof which are illustrated in the appended drawings.

DETAILED DESCRIPTION OF THE PREFERRED EMBODIMENTS

OVERVIEW OF THE SYSTEM

Figure 1:
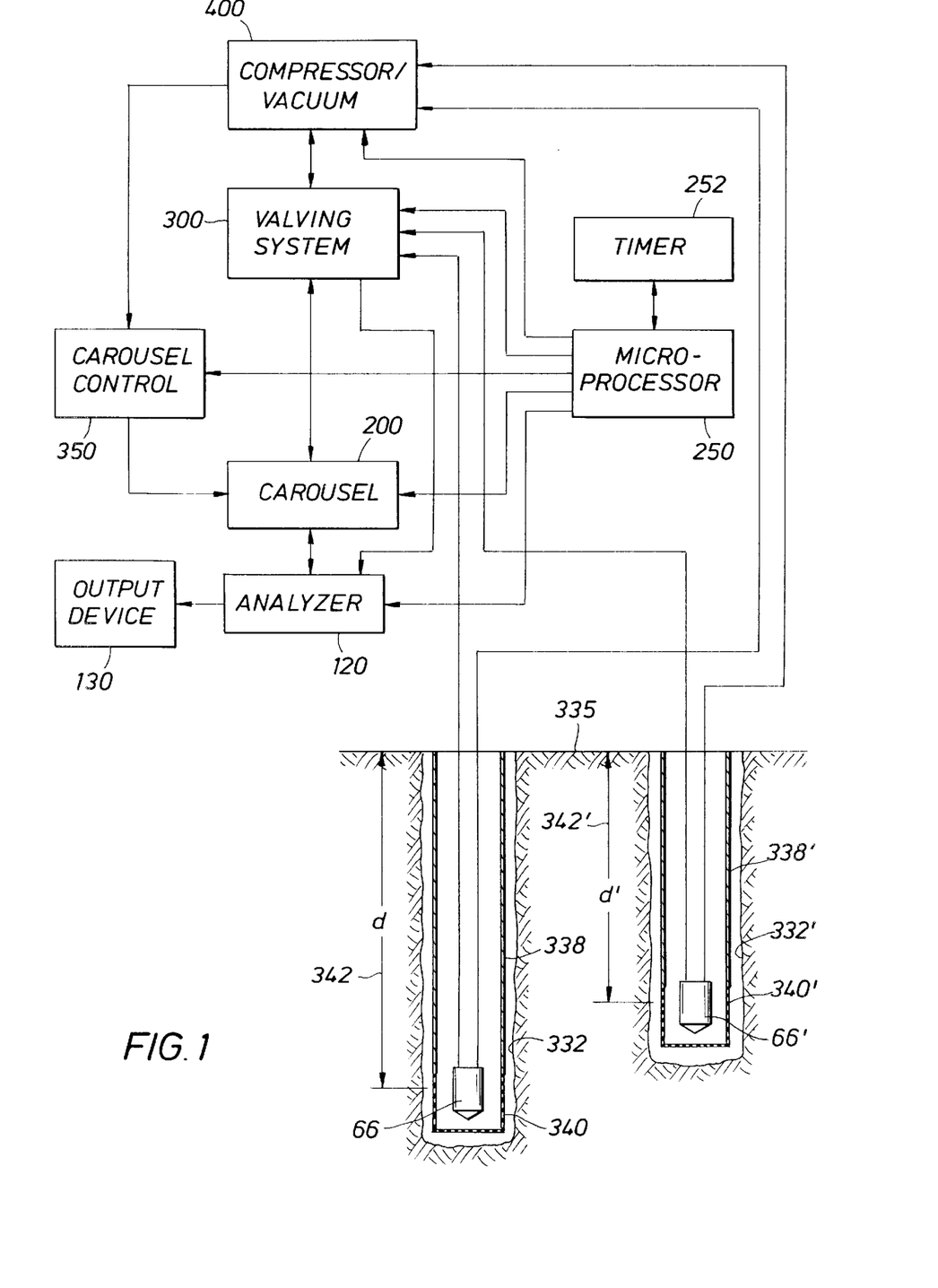
FIG. 1 is a functional block diagram of the sampling and pretreatment system, and illustrates how this system cooperates with an analyzer.

FIG. 1 represents a functional diagram of the sampling and pretreating system which cooperates with a tritium analyzer.

The system is depicted in FIG. 1 as gathering samples from two wells 332 and 332'. Each well is preferably lined or "cased" with a steel, plastic or composite liner 338 and 338' to prevent the respective boreholes from caving in. Near the bottom of the casings 338 and 338', perforated screens 340 and 340' are affixed to aid the flow of water from the surrounding ground formations through the boreholes of the respective monitor wells. Monitor wells are of preferably differing depths d and d', where these dimensions are denoted by the numerals 342 and 342', respectively. A submersible pump 66 is positioned within the well 332 in the region of the liner 66. Likewise, a submersible pump 66' is positioned within the well 332' in the vicinity of the screen 340'. It should be understood that the invention is not limited to monitoring two wells, but can be used to monitor only one well, or a plurality of wells greater than two. Furthermore, the invention is not limited to monitoring water which flows into well boreholes, but can also be used to monitor water in cooling ponds, canals, lakes and the like.

Still referring to FIG. 1, each pump 66 and 66' cooperates with a compressor/vacuum pump system 400 which is used to fill the pumps with liquid sample, and then to transfer these samples to the surface for pretreating and analysis. The compressor/vacuum pump system cooperates with a valving system, which also includes flow lines, denoted by the block 300. Specifics of the operation of the valving system 300 will subsequently presented in detail. At this point in the disclosure, it suffices to say that the valving system 300 is used to control the flow of the sample liquid, and the flow of purge air and wash water for the system.

Still referring to FIG. 1, the valving system cooperates with a carousel mechanism 200 which holds a plurality of columns in which sample water is pretreated prior to analysis. The carousel mechanism is operated mechanically by cylinders and piston devices powered by the compressor vacuum pump system 400 under the control of a carousel controller 350.

Once each collected water sample has been treated in a specific column carried by the carousel mechanism 200, the sample is then passed to an analyzer 120 for analysis by means of the valving system 300 and its accompanying flow lines. If the sampled liquid is water and the contaminant to be measured is tritium, a chromatographic analyzer such as a Radiomatic HPLC high precision liquid chromatographic unit manufactured by Hewlett Packard can be used as the analyzer 120. Results are displayed with an appropriate analog or digital meter (not shown), printed by means of a printer (not shown), or recorded on a magnetic disk (not shown) or other digital recording device.

Again referring to FIG. 1, all of the previously discussed elements of the system, with the exception of the submersible pumps 66 and 66' and some elements of the valving system and flow lines, are preferably located at the surface of the earth 335. Furthermore, the compressor/vacuum system 400, the valving system 300, the carousel 200 and the carousel controller 350 are preferably controlled by a microprocessor 250 and a timer 252. Stated another way, the sequence of events described briefly above and described in detail in subsequent sections, are preferably implemented by a programmed microprocessor 250 and timer 252. The timing of the analyzer 120 is preferably independent of the microprocessor 250 and timer 252. The microprocessor 250 does, however, send signals to the analyzer 120 at a point in time when each gathered sample has been pretreated and is ready for acceptance by the analyzer 120 for analysis for contaminants such as tritium.

PRETREATMENT SAMPLE COLUMN

Figure 2:
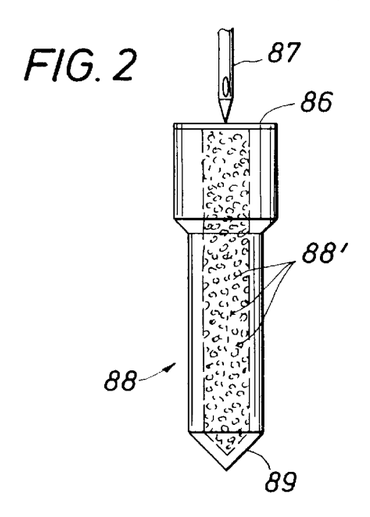
FIG. 2 illustrates the major elements of a sample pretreatment column.

FIG. 2 illustrates a sample pretreatment column identified by the numeral 88. The column is filled with a plurality of resins, illustrated conceptually and identified with the numeral 88', which are selected and designed to remove certain cations and other contaminants from the water sample which would tend to introduce error in the subsequent tritium concentration when the pretreated sample is passed to the tritium analyzer 120 (see FIG. 1). Each column is sealed at an upper end 86 and a lower end 89 to prevent contamination of the water packed resins prior to pretreating sample. Referring to both FIG. 1 and FIG. 2, one sample pretreatment column in mounted within the carousel 200 for each sample acquired and analyzed. Sample from the submersible pump 66 within the well being sampled is passes through a valving system and through the flow line 85 and through a hollow needle 87 which penetrates the upper end 86 of the column housing 88 as described in this disclosure and drawings. Sample fluid is pumped through the column 88 and out through the lower end 89 after it has been removed or "broken" by mechanical actions likewise described in a subsequent section. The pumping of sample liquid through the column 86 constitutes the pretreatment of the sample prior to analysis for tritium. Sample pretreatment columns suitable for this purpose are manufactured by the Iomega Corporation.

THE CAROUSEL MECHANISM

Figure 3A:
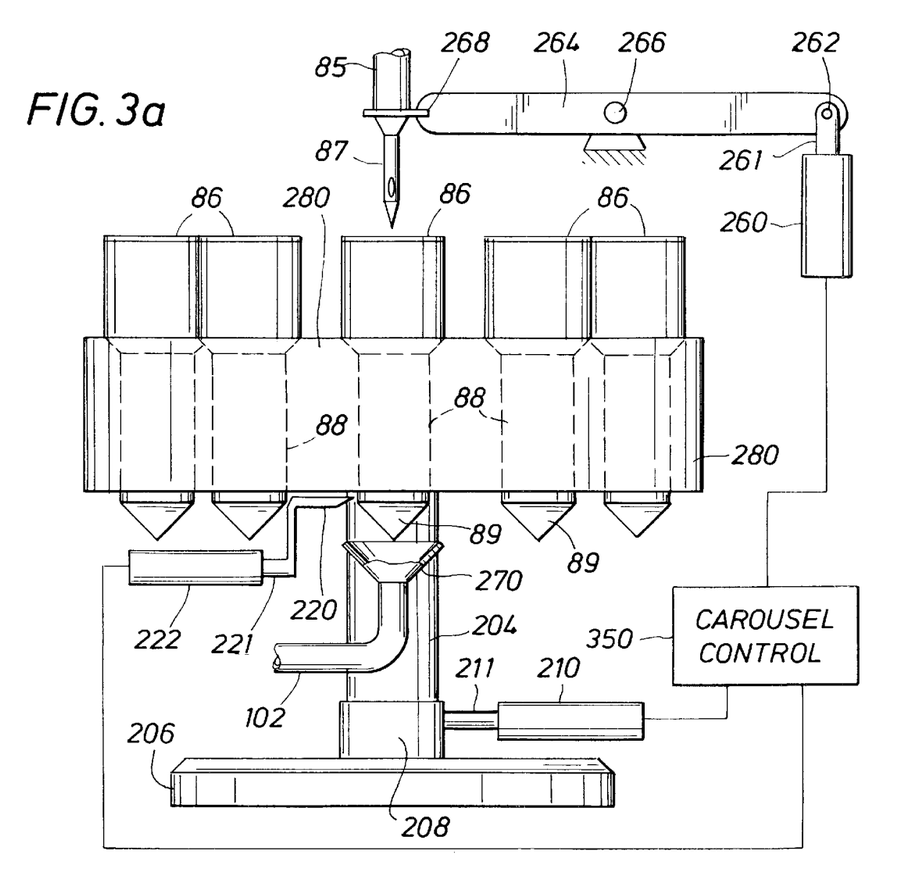
FIG. 3a is a side view of the carousel mechanism.

A side view of the carousel mechanism is shown in FIG. 3a. A tray 280 holds a plurality of sample pretreatment columns 88. The preferably circular tray 280 can rotate about a support column 204 which is affixed to a support base 206. One arrangement for the sample pretreatment columns 88 in the tray 280, and the position of the support column 204, are better shown in the abbreviated top view of the carousel mechanism shown in FIG. 3b.

Referring again to FIGS. 3a and 3b, the tray 280 is rotated such that each sample pretreatment column 88 is sequentially positioned immediately below a hollow needle 87 and immediately above a functionally illustrated flow receptacle 270 which is connected to a flow line 102. The tray 280 is rotated by a ratchet assembly 208 which cooperated with a pneumatic piston 211 and cylinder 212. Compressed air is supplied to the piston/cylinder assembly through the carousel controller 350 which cooperates with the compressor/vacuum system 400.

Figure 3B:
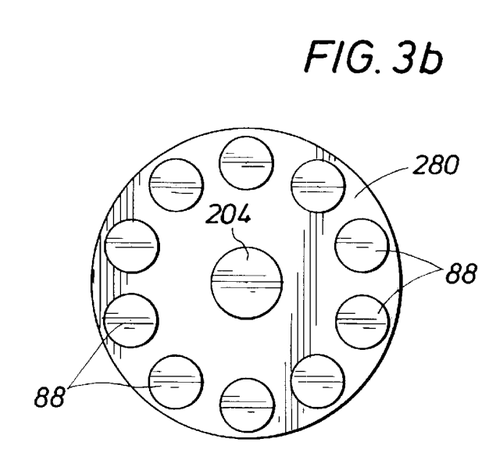
FIG. 3b is an abbreviated top view of the carousel mechanism.

Once a sample pretreatment column 88 is in place, it is necessary to pump sample water through the column in order to obtain the desired pretreatment of the sample. Recalling that each column is sealed to avoid contamination before use, it is necessary to establish a fluid flow path through the properly positioned column 88. The upper end 86 of the column is penetrated by moving the hollow needle 87 downward by the activation of a pneumatic piston 261 and cylinder 260. Again, compressed air is supplied to this piston/cylinder assembly through the carousel controller which cooperates with the compressor/vacuum system 400. The piston is attached to a lever 264 at position 262 by means of a swivel. The lever pivots about a point 266, and the left side of the lever is attached by means of a swivel to a bracket 268 affixed to the hollow needle 87. When activated, the piston 261 moves upward thereby driving the hollow needle 87 through the top 86 of the column 88. The bottom tip 89 of the column is sheared or broken by the action of a tip breaking cutter 220 which is attached to a pneumatic piston 221 cooperating with the pneumatic cylinder 222. Once again, compressed air is supplied to the piston/cylinder assembly through the carousel controller 350 which cooperates with the compressor/vacuum system 400. When activated, the piston 221 and attached cutter 220 move to the right thereby breaking the tip 89 of the column 88 and establishing a flow path through the column and resins 88' contained within. Fluid leaving the column is collected by a flow receptacle which is shown functionally as the element 270. Pretreated sample the flows through a flow line 102 to the analyzer 120. The tray 280 is then rotated such that the next column is positioned for sample flow through. It is emphasized the mechanisms used to rotate the tray 280, to penetrate the top 86 of the column 88, and to break the lower tip 89 of the column 88 are functional illustrations for brevity and clarity, and that other pneumatically powered mechanical arrangements and devices are equally suited to perform these tasks.

PUMP OPERATION, PRETREATMENT AND ANALYSIS SEQUENCE

Figure 4:
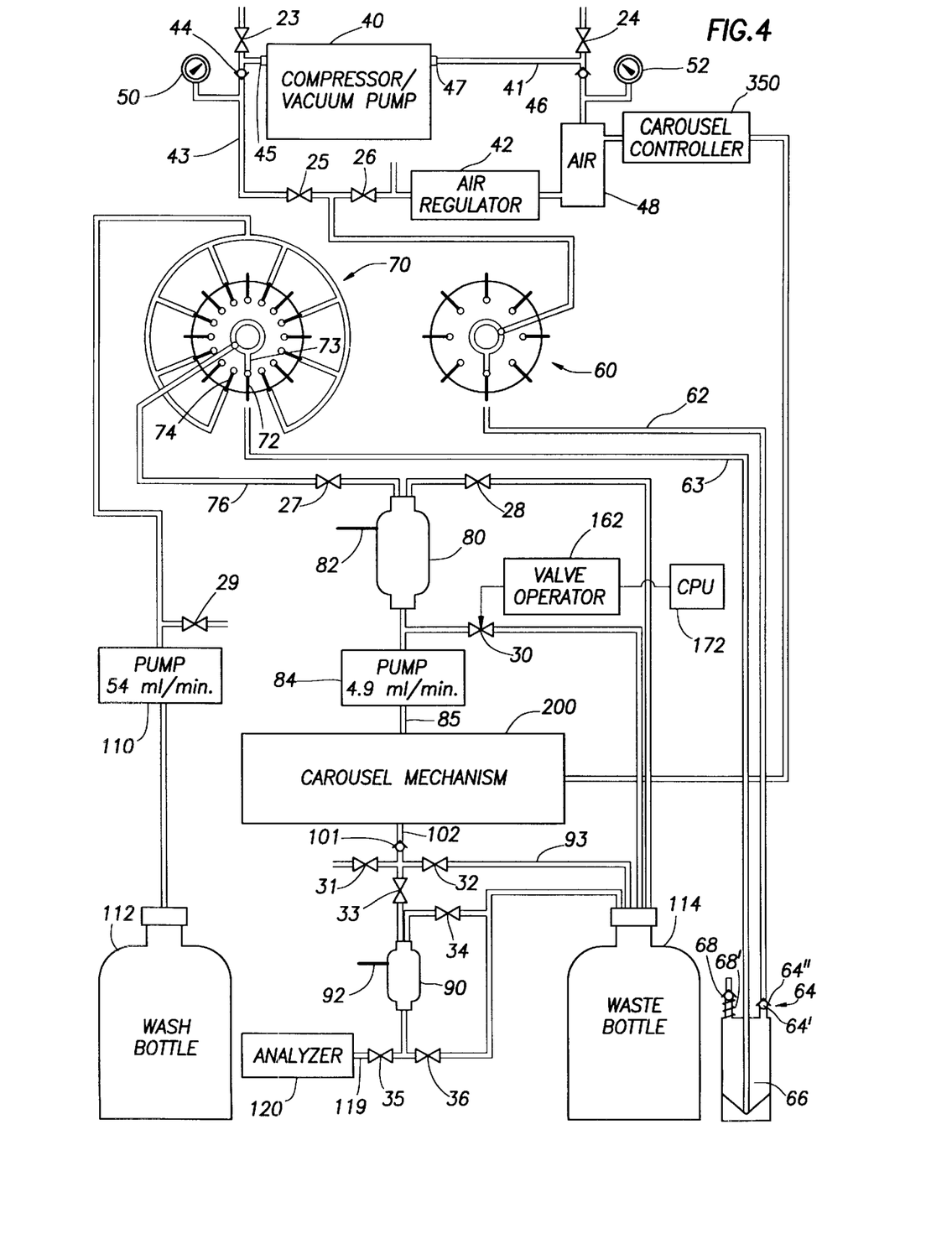
FIG. 4 is a more detailed illustration of the sampling and pretreatment system cooperating with an analyzer.

An illustration of the sampling sequence for a given well will now be disclosed in detail. FIG. 4 illustrates the sampling system in more detail, and will be used heavily in the coming illustration. FIG. 4, however, does not show the system microprocessor 250 and timer 252 (see FIG. 1) in order to enhance the clarity of FIG. 4. It should be understood, however, that certain elements cooperate with the timer and microprocessor as specified in previous and subsequent discussion.

In detailing the operation of the apparatus, it will be assumed that eight wells are to be monitored, and that a well designated as well No. 5 is currently being sampled. The system is configured to sample eight wells, and configured to be in the process of sampling well No. 5, is shown in FIG. 4. Wells No. 1 through 4 have been sampled, and wells No. 6–8 remain to be sampled in the illustrated sample sequence. It should be understood, however, that the apparatus can be tailored to monitor fewer than eight wells or more than eight wells. It should also be understood that cooling ponds or canal, rather than wells, can likewise be monitored, and that wells, ponds, canals and the like can be monitored at varying depths as will be discussed further in a subsequent section of this disclosure.

Initiation of the Sequence for a Given Well

Referring to FIG. 4, a pump 40 of the compressor/vacuum system 400 serves as both a compressor and a vacuum pump in the operation of the system, Upon start-up of the sampling and pretreating procedure, the pump 40 is activated and a valve 24, which vents the compressor line 41 of the pump 40, is in the closed position. Air is drawn into the pump 40 through a vent valve 23, which is in the open position, and into a vacuum side 45 of the pump 40. Air compressed by the action of the pump 40 flows out through a compression side 47 and into an air tank 48 by means of line 41. A check valve 46 prevents air flowing from the air tank 48 back toward the pump 40. Pressure within the air tank 48, which is indicated by a gauge 52, is allowed to reach approximately 100 psi. As was explained in detail in a previous section, compressed air within the air tank 48 is used to rotate the carousel mechanism 200 used to transport the pretreatment sample columns, to penetrate the tops of these columns to receive sample liquid, and to remove the bottoms of these columns to allow sample to flow eventually to the sample analyzer 120 to be analyzed for tritium concentration. Compressed air is also used to transfer samples collected by the submersible pump 66 to the surface of the earth.

FILLING THE SUBMERSIBLE PUMP

Figure 5A:
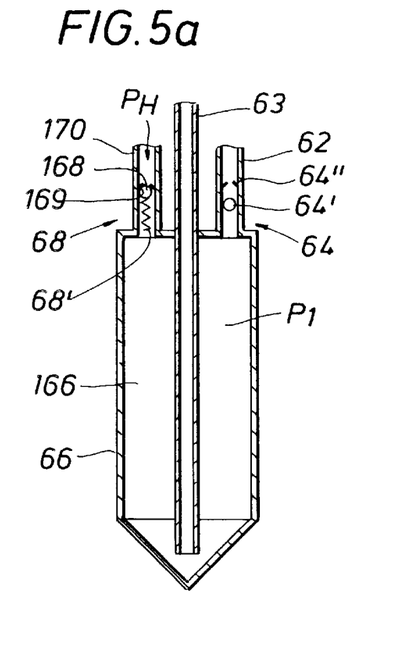
FIG. 5a illustrates the valve settings and flow paths of the submersible pump prior to filling with liquid.

FIG. 5a depicts the submersible pump 66 prior to filling with liquid. The pump is submerged within a liquid with a head pressure $P_h$. A pump inlet 170 is closed to the external liquid by means of a check valve 68. More specifically, a spring 68' forces a ball 168 against a seat 169 thereby closing the valve 68 and preventing liquid from flowing into the pump chamber 166. The pressure at which the check valve 68 opens will be referred to as the "cracking" pressure and will be represented symbolically as $P_c$. A hydro check valve 64 is connected to the line 62, and is shown in the open position with the ball 64' being displaced from the seat 64". The line 62 here represents a control inlet to the pump since both vacuum and pressure are applied to this inlet. $P_1$ represents the pressure within the pump chamber 166 in the status shown in FIG. 5a. Mathematically, for the pump in the status shown in FIG. 5a, $P_c > P_h - P_1$.

Figure 5B:
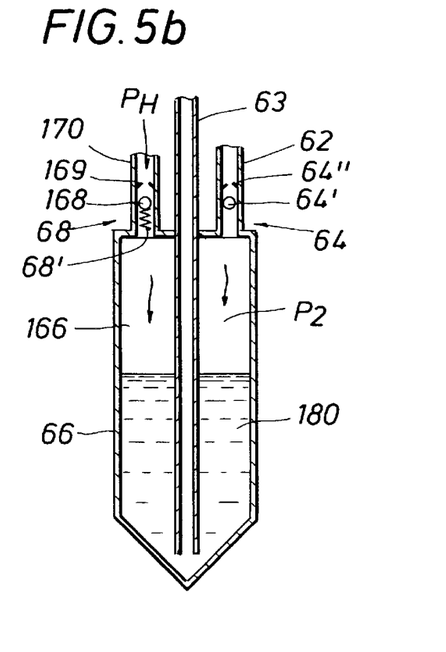
FIG. 5b illustrates the valve settings and flow paths of the submersible pump during filling.

Attention is next directed to FIG. 5b and again to FIG. 4. FIG. 5b depicts the pump chamber 166 being filled with a liquid 180. A vacuum is applied to the control inlet of the submersible pump 66 by means of the line 62. Valve 23 on the vacuum side 45 of pump 40 is closed. Valve 25 is opened, and valve 26 is closed thereby applying a vacuum, which is monitored with a gauge 50, to an eight position rotary valve of the type manufactured by Valco Instruments, Inc. of Houston, Tex. The vent valve 24 on the compressor side 47 of the pump 40 is opened. Recalling that the sampling of well No. 5 is being used as an example, the valve 60 is positioned to transfer the applied vacuum through line 62 to a hydro check valve 64 mounted on the pump 66. At this point in the sampling sequence, the internal pump pressure within the chamber 166 is defined as $P_2$, where $P_2 < P_1$. Liquid 180 from the well bore (see FIG. 1) then flows into the pump chamber 166 through the inlet 170 and the opened check valve 68, as indicated by the flow arrows, and begins to fill the pump reservoir. The valve 68 is opened when the head pressure $P_h$ forces the ball 168 away from the seat 169. This occurs when $P_h > P_c - P_2$. The term "vacuum" is used to indicate a substantially reduced pressure that is provided at the control inlet of the pump, and in the pump chamber 166, by the compressor/vacuum system 400. No absolute units are associated with the term. It suffices to define vacuum, in the context of this disclosure, as the pressure $P_2$ at which $P_h > P_c - P_2$.

Figure 5C:
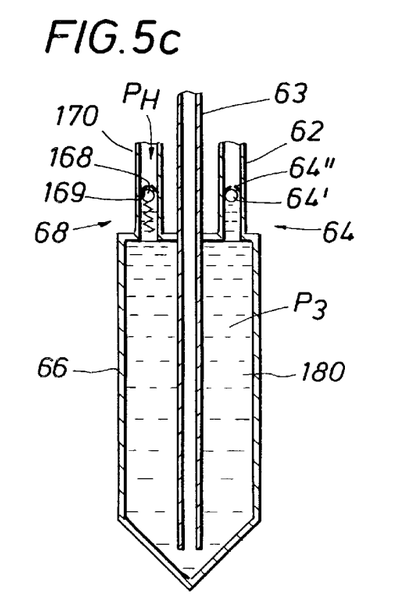
FIG. 5c illustrates the valve settings of the submersible pump when filled with liquid.

FIG. 5c shows the reservoir of the pump 66 filled with liquid 180. When the liquid level within the chamber reaches the hydro check valve 64, the ball 64' floats and is therefore pressed against the seat 64" thereby closing the control inlet and isolating the pump from the vacuum in line 62. At this point, the internal pressure in the pump chamber is $P_3$, where $P_3 > P_2$. Recall that the check valve 68 is spring loaded to open only at or above a predetermined cracking pressure $P_c$. This cracking pressure must be greater than the head pressure seen by the pump 66 when placed at a given depth minus the internal pump pressure. The check valve 68 is, therefore, closed when the pump is in the status shown in FIG. 5c since $P_c > P_h - P_3$.

Again, the spring 68' closes the valve 68. This prevents flow of sample liquid into the pump while vacuum is applied at the control inlet hydro check valve 64, and also the head pressure $P_h$ minus the internal pressure of the pump under vacuum ($P_2$) exceeds the cracking pressure $P_c$. Valves that are available commercially and that are suitable for use as the valve 68 are available in four cracking pressures which are ⅓, 1, 10, and 25 pounds per square inch gauge (psig). The following chart shows the maximum depth that the pump can be immersed in water for each different cracking pressure for the valve 68.

| Cracking Press. (psig) | Max. Depth (feet) |
| --- | --- |
| 1/3 | 1/2 |
| 1 | 2 |
| 10 | 20 |
| 25 | 50 |

Evacuating the Submersible Pump

Figure 5D:
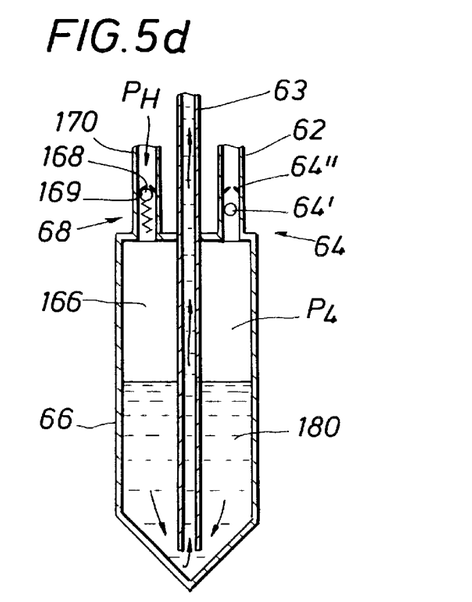
FIG. 5d illustrates the valve setting and flow paths for purging of sample liquid from the submersible pump to the surface for analysis.

Attention is now drawn to FIG. 5d and again to FIG. 4. Once the pump chamber 166 is filled with sample liquid 180, it is necessary to retrieve this sample at the surface of the earth by evacuating the pump. Valve 25 is closed to isolate the pump 66 from the vacuum side 45 of the pump 40. Valve 23 is opened and valve 24 is closed thereby supplying compressed air to the valve 60, through the open valve 26, from the air tank 48 and an air regulator 42. The pressure within the air tank 48 is monitored with a gauge 52. The air regulator 42 is preferably such that the pressure at the open valve 26, and correspondingly at the well No. 5 position of the valve 60, is approximately 25 psi or a pressure great enough to lift the sample. Compressed air is then transferred through line 62 to the control inlet of the pump, through the hydro check valve 64, and into the interior of the pump 66. The ball 64' is displaced from the seat 64" thereby opening the hydro check valve 64 when pressure is applied to the control inlet by means of line 62. The valve 68 remains closed since the internal pump pressure $P_4$ is now greater than the liquid head pressure $P_h$. Sample liquid 180 within the pump 66 is forced upward through a line 63 in a flow path indicated by the arrows. This displaced liquid sample flows to a sample intake position of a sixteen position valve 70 of the type manufactured by Valco Instruments, Inc. of Houston, Tex. The captured sample liquid is thereby transferred from the downhole pump 66 to the surface of the earth for evaluation. The sample volume is consistent over many samples.

Filling Reservoir Prior to Pretreatment

Sample fluid is displaced from the pump 66 and flows through the valve 70. Again referring to FIG. 1, valve 27 is open and valve 28 is closed so that sample fluid flows out of the valve 70 through the flow line 76 into a reservoir 80. The preferred volume of sample deposited into the reservoir 80 is approximately 50 cubic centimeters (cc), and this volume is verified by a capacitive proximity switch 82. Once the chamber 80 is filled with sample liquid, the valve 27 is closed while the valve 28 remains open. The sample liquid within the reservoir 80 is now ready to be pretreated.

Pretreating the Sample and Transfer to the Analyzer

A sample pretreatment column 88 is positioned by the carousel mechanism 200, as described previously, for sample pretreatment. Referring now to FIGS. 4 and 3a, the desired column positioning is obtained by rotating the carousel tray 280 by the activation of the pneumatic cylinder 210 and cooperating piston 211. The top 86 of the positioned column 88 is penetrated by the hollow needle 87 by activating the pneumatic cylinder 260 and cooperating piston 261. The bottom tip 89 of the positioned column 88 is broken by the activation of the pneumatic piston 221 and cooperating cylinder 222. Compressed air to activate these pneumatic devices is supplied from the air tank 48 under control of the carousel controller 350.

Still referring to FIGS. 4 and 3a, sample fluid is now able to be pumped by a pump 84 from the reservoir 80 through a flow line 85, through the hollow needle 87, through the resins 88' contained within the column 88, out the bottom of the column 88, through the flow receptacle 270, through the flow line 102 and through the check valve 101. The pump 84 operates preferably at a rate of 4.9 milliliters per minute (ml/min). Valve 32 is opened and valves 31 and 33 are closed so the approximately 10 cc of the 50 cc of sample contained in the reservoir 80 is pumped through a flow line 93 into a waste bottle 114. This purges the valve 101 of any contaminants from the previous sample. This requires approximately two minutes. Valve 31 is then opened briefly to puree the flow line 93 of any liquid by using dry air from a purge gas source (not shown). This purge flows to the waste bottle 114.

Referring to FIGS. 1, 3a and 4, valves 31 and 32 are then closed and valves 33 and 34 are opened. Approximately 10 ml of sample fluid are then pumped by the pump 84 into a sample holder 90, with the 10 ml volume being confirmed by the capacitive proximity switch 92. When the sample holder is filled with the desired 10 ml of sample fluid, the valve 33 is closed and valve 34 remains open. A signal is then sent to the system microprocessor 250 indicating that the sample container 90 holds a sample which has been pretreated and which is now ready to be analyzed for tritium content by the analyzer 120. Furthermore, a communication channel signifies that the sample is from a given source, which in the example being discussed is well No. 5. Valve 35 is then opened and the sample stored in the sample chamber 90 is flowed through the valve 35 and through the flow line 119 to the analyzer 120 for analysis.

Purging of the System

After each sample acquisition, pretreatment and analysis, the system must be purged so that the next sample will not be contaminated by remnants of the previous sample.

Referring to FIG. 4, the valves 27, 28 and 29 are opened and purge gas, preferably dry air from a purge gas source (not shown), is introduced through opened valve 29. This effectively clears the sample position conduit 72 of the valve 70 for the well being sampled (well No. 5 in this example), the flow line 76, the sample chamber 80, and other connecting lines shown in FIG. 4. The purge gas and any remaining liquid samples is driven to the waste bottle 114. The valves 32, 33, 34, and 36 are then opened, the valve 35 is closed, and purge air is introduced through the open valve 31 thereby purging remnant liquid sample from flow line 93 and from the sample chamber 90 into the waste bottle 114.

Next, appropriate elements of the system are washed with preferably deionized water to further remove traces of the prior sample in order to avoid contaminating the next sample. Still referring to FIG. 4, the valves 29, 30, 33 and 31 are then closed, and the valve 32 is opened. The sixteen position valve 70 is then rotated, by the pneumatic system previously described, one position (counter clockwise as shown in FIG. 4) such that the wash position conduit 74 for well No. 5 is aligned with the main flow conduit 73. Next, preferably deionized water is pumped from a wash bottle reservoir 112 by means of a pump 110 through the valve 70, the flow line 76, the chamber 80, the pump 84, the column 88, and the flow line 93 into the waste bottle 114. The pump 110 operates at preferably 64 ml/min. With the above valve settings, approximately 20 cc of deionized water are pumped to flush the chamber 80 and the column 88. Next, valves 32, 36 and 31 are closed, valves 33, 34, and 36 are opened, and the deionized water is pumped through the sample bottle 90 and adjacent flow lines and deposited into the waste bottle 114. Finally, purge gas, preferably again from the source (not shown) of dry air, is flowed through all elements washed with deionized water by sequentially opening the appropriate valves as depicted in FIG. 4.

After completing the sample gathering, pretreating, sample analysis and system purge operations, the carousel tray 280 is rotated, using previously described apparatus and methods, such that a fresh column 88 is positioned for the treatment of the next sample. Likewise, the valves 60 and 70 are positioned for the next sample, which will be a sample from well No. 6 in the example being discussed.

While the foregoing disclosure is directed toward preferred embodiments, the scope of the invention is set forth by the claims which follow.

What is claimed is:

1. A submersible pump comprising:
   (a) a chamber;
   (b) an inlet port connected to said chamber and controlled by a check valve; and
   (c) a control port connected to said chamber, wherein said chamber is filled with liquid in which said pump is submerged when
      (i) a vacuum applied to said control port creates a reduced pressure within said chamber, and
      (ii) said liquid in which said pump is submerged exerts a pressure at said check valve sufficient to open said check valve thereby allowing said liquid to flow into said chamber.

2. The submersible pump of claim 1 further comprising:
   (a) a hydro check valve controlling flow through said control port; and
   (b) an outlet port connected to said chamber, wherein said hydro check valve closes said control port when said chamber fills with said liquid thereby
       (i) isolating said chamber from said vacuum,
       (ii) increasing pressure within said chamber, and
       (iii) closing said check valve.

3. The submersible pump of claim 2 further comprising an outlet port connected to said chamber, wherein liquid contained within said chamber is purged by applying pressure to said control port thereby:
   (a) opening said hydro check valve;
   (b) further increasing pressure within said chamber;
   (c) continuing to hold said check valve closed; and
   (d) forcing said liquid to flow from said chamber through said outlet port.

4. The submersible pump of claim 2 wherein said hydro check valve comprises:
   (a) a ball which is buoyant within said liquid; and
   (b) a seat,
wherein said check valve is closed when the level of liquid within said chamber rises sufficiently to press said buoyant ball against said seat.

5. The submersible pump of claim 1 wherein said check valve comprises:
   (a) a ball;
   (b) a seat; and
   (c) a spring which retains said ball against said seat as long as said check valve is exposed to liquid head pressure less than a cracking pressure of said check valve.

6. The submersible pump of claim 5 wherein said cracking pressure is predetermined by the force exerted upon said ball by said spring and said check valve opens at a pressure which exceeds the difference of said cracking pressure of said check valve and pressure within said chamber.

7. A submersible pump system comprising:
   (a) a submersible pump; and
   (b) a compressor/vacuum system cooperating with said submersible pump, wherein said submersible pump comprises
       (i) a chamber,
       (ii) an inlet port connected to said chamber and controlled by a first check valve,
       (iii) a control port connected to said chamber and controlled by a second check valve, and
       (iv) an outlet port connected to said chamber,
wherein said chamber is filled with liquid in which said pump is submerged by applying a vacuum by said compressor/vacuum system to said control port thereby reducing pressure within said chamber such that the differential pressure across said first check valve is greater than a cracking pressure of said first check valve.

8. The submersible pump system of claim 7 wherein said differential pressure comprises the head pressure of the liquid within which said pump is submerged minus the difference of said cracking pressure of said first check valve and internal chamber pressure.

9. The submersible pump system of claim 7 wherein said second check valve closes when said chamber fills with liquid thereby:
   (a) isolating said chamber from said vacuum;
   (b) increasing pressure within said chamber; and
   (c) closing said first check valve.

10. The submersible pump system of claim 9 wherein liquid contained within said chamber is purged by applying pressure by means of said compressor/vacuum system to said control port thereby:
    (a) opening said second check valve;
    (b) further increasing pressure within said chamber;
    (c) continuing to hold said first check valve closed; and
    (d) forcing liquid to flow out of said chamber through said outlet port.

11. The submersible pump system of claim 7 wherein said second check valve comprises:
    (a) a ball which is buoyant within said liquid; and
    (b) a buoyant ball seat,
wherein said second check valve is closed when the level of liquid within said chamber rises sufficiently to press said buoyant ball against said buoyant ball seat, and wherein said first check valve comprises:
    (c) a ball;
    (d) a seat; and
    (e) a spring which retains said ball against said seat as long as said first check valve is exposed to liquid head pressure less than said cracking pressure of said first check valve, and wherein said cracking pressure is predetermined by the selection of the force exerted upon said ball by said spring.

12. A method for acquiring liquid sample from a reservoir comprising the steps of:
    (a) providing a submersible pump comprising an inlet port controlled by a first check valve, a control port, and a chamber;
    (b) applying a vacuum to said control port thereby creating a reduced pressure within said chamber, and
    (c) flowing liquid, within which said pump is submerged, into said chamber when a head pressure exerted by said liquid opens said first check valve by exceeding the difference of a cracking pressure of said first check valve and said reduced chamber pressure.

13. The method of claim 12 further comprising the steps of:
    (a) providing a second check valve within said control port;
    (b) providing an outlet port connected to said chamber; and
    (c) closing said second check valve when said chamber fills with liquid thereby
        (i) isolating said chamber from said vacuum,
        (ii) increasing pressure within said chamber, and
        (iii) closing said it check valve.

14. The method of claim 13 further comprising the step of purging liquid contained within said chamber by applying pressure to said control port thereby:
    (a) opening said second check valve;
    (b) further increasing pressure within said chamber;
    (c) continuing to hold said first check valve closed; and
    (d) forcing liquid to flow out of said chamber through said outlet port.

15. The method of claim 14 comprising the additional step of providing a source of compressed gas at the surface of the earth and transferring said compressed gas source to said submerged pump to force liquid to flow out of said chamber through said outlet port.

16. The method of claim 14 including the additional step of flowing said liquid from said outlet port to an analyzer.

17. The method of claim 16 wherein said analyzer is above said reservoir and at the surface of the earth.

18. The method of claim 13 wherein said second check valve comprises a ball which is buoyant within said liquid and adjacent to a seat; and wherein said second check valve is closed when the level of liquid within said chamber rises sufficiently to press said buoyant ball against said seat.

19. The method of claim 12 wherein said first check valve comprises a ball, seat and spring wherein said ball is retained against said seat as long as said first check valve is exposed to liquid head pressure less than the cracking pressure of said first check valve.

20. The method of claim 19 including the additional step of setting said cracking pressure at a predetermined value by the force exerted upon said ball by said spring.

21. The method of claim 12 further comprising the step of providing a vacuum source at the surface of the earth and transferring said vacuum source to said submerged pump to fill said chamber.

22. A method for acquiring a plurality of liquid samples from a reservoir comprising the steps of:
(a) providing a plurality of submersible pumps, each of which comprises a chamber, an inlet port controlled by a first check valve and connected to said chamber, and a control port connected to said chamber;
(b) applying a vacuum from a vacuum source to each said control port thereby creating a reduced pressure within each said chamber, and
(c) flowing liquid, within which each said pump is submerged, into each said chamber when head pressure exerted by said liquid opens each said first check valve by exceeding the difference of a cracking pressure of each said first check valve and said reduced pressure with each said chamber, thereby obtaining a sample of liquid exerting said head pressure.

23. The method of claim 22 including the additional step of setting the cracking pressure of each said first valve to a different value.

24. The method of claim 22 including the additional steps of:
(a) positioning each said pump at a different depth within said reservoir; and
(b) setting the cracking pressure of each said first check valve to a value proportional to the head pressure of said liquid at the depth at which each said pump is positioned.

25. The method of claim 22 comprising the additional steps of:
(a) providing a second check valve within each said control port;
(b) providing a plurality outlet port, wherein an outlet port is connected to each said chamber; and
(c) closing each said second check valve when each said chamber fills with liquid thereby
(i) isolating each said chamber from said vacuum,
(ii) increasing pressure within each said chamber, and
(iii) closing each said first check valve.

26. The method of claim 25 further comprising the step of purging liquid contained within each said chamber by applying pressure to each said control port thereby:
(a) opening each said second check valve;
(b) further increasing pressure within each said chamber;
(c) continuing to hold said each first check valve closed; and
(d) forcing liquid to flow out of each said chamber through each said outlet port there attached.

27. The method of claim 26 including the additional step of flowing said liquid from each said outlet port to an analyzer.

28. The method of claim 27 including the additional step of flowing said liquid to said analyzer, wherein said analyzer is above said reservoir and at the surface of the earth.

29. The method of claim 27 including the additional step of flowing liquid containing tritium to said analyzer, wherein said analyzer responds to the concentration of tritium within said liquid.

30. A submersible pump system comprising:
(a) a plurality of submersible pumps; and
(b) a compressor/vacuum system cooperating with each said submersible pump,
wherein each said submersible pump comprises
(i) a chamber,
(ii) an inlet port connected to said chamber and controlled by a first check valve,
(iii) a control port connected to said chamber and controlled by a second check valve, and
(iv) an outlet port connected to said chamber,
wherein said chamber is filled with liquid in which each said pump is submerged by applying a vacuum by said compressor/vacuum system to each said control port thereby reducing pressure within each said chamber such that the differential pressure across each said first check valve is greater than a cracking pressure of each said first check valve.

31. The submersible pump system of claim 30 wherein said differential pressure comprises the head pressure of the liquid within which said each pump is submerged minus the difference of cracking pressure of each said check valve and internal pressure within each said chamber.

32. The submersible pump system of claim 31 wherein each said second check valve closes when each said chamber fills with liquid thereby:
(a) isolating said chamber from said vacuum;
(b) increasing pressure within said chamber; and
(c) closing said first check valve attached thereto.

33. The submersible pump system of claim 32 wherein liquid contained within each said chamber is purged by applying pressure by means of said compressor/vacuum system to each said control port thereby:
(a) opening each said second check valve;
(b) further increasing pressure within said chamber;
(c) continuing to hold said first check valve closed; and
(d) forcing liquid to flow out of said chamber through said outlet port attached thereto.

34. The submersible pump system of claim 33 wherein each said second check valve comprises:
(a) a ball which is buoyant within said liquid; and
(b) a buoyant ball seat,
wherein said second check valve is closed when the level of liquid within each said chamber rises sufficiently to press said buoyant ball against said buoyant ball seat, and wherein each said first check valve comprises:
(c) a ball;
(d) a seat; and
(e) a spring which retains said ball against said seat as long as said first check valve is exposed to liquid head pressure less than said cracking pressure of said first check valve, and wherein said cracking pressure is predetermined by the selection of the force exerted upon said ball by said spring.

35. The submersible pump system of claim 30 wherein said compressor/vacuum system is located at the surface of the earth.

36. The submersible pump system of claim 30 further comprising a controller, wherein said controller cooperates with said compressor/vacuum system to supply said vacuum to each said submersible pump in a controlled sequence.

37. The submersible pump system of claim 36 wherein said controller is located at the surface of the earth.

38. The submersible pump system of claim 36 wherein said controller controls the flow of liquid from each said submersible pump to an analyzer.

39. The submersible pump system of claim 38 wherein said controller controls the flow of liquid containing tritium from each said submersible pump to said analyzer, wherein said analyzer responds to the concentration of tritium in said liquid.

40. The submersible pump system of claim 30 wherein said cracking pressure of each said first valve is set at a value varying between about ⅓ pounds per square inch and about 25 pounds per square inch.

* * * * *